United States Patent
Duefert et al.

(10) Patent No.: US 10,077,223 B2
(45) Date of Patent: Sep. 18, 2018

(54) METHOD FOR PRODUCING MONOETHYLENE GLYCOL

(71) Applicant: BASF SE, Ludwigshafen am Rhein (DE)

(72) Inventors: Alexander Duefert, Ludwigshafen (DE); Rolf Pinkos, Bad Duerkheim (DE); Michael Reiser, Kaiserslautern (DE); Philipp Brüggemann, Erlangen (DE); Gerhard Theis, Maxdorf (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/747,809

(22) PCT Filed: Jul. 26, 2016

(86) PCT No.: PCT/EP2016/067706
§ 371 (c)(1),
(2) Date: Jan. 26, 2018

(87) PCT Pub. No.: WO2017/017074
PCT Pub. Date: Feb. 2, 2017

(65) Prior Publication Data
US 2018/0222830 A1    Aug. 9, 2018

(30) Foreign Application Priority Data

Jul. 29, 2015 (EP) .................... 15178919

(51) Int. Cl.
| | |
|---|---|
| *C07C 27/04* | (2006.01) |
| *C07C 29/149* | (2006.01) |
| *B01J 23/84* | (2006.01) |
| *B01J 23/843* | (2006.01) |
| *B01J 23/888* | (2006.01) |
| *C07C 67/08* | (2006.01) |
| *B01J 23/72* | (2006.01) |
| *B01J 21/02* | (2006.01) |
| *C07C 31/20* | (2006.01) |
| *C07C 29/90* | (2006.01) |

(52) U.S. Cl.
CPC ............ *C07C 29/149* (2013.01); *B01J 21/02* (2013.01); *B01J 23/72* (2013.01); *C07C 29/90* (2013.01); *C07C 31/202* (2013.01); *C07C 67/08* (2013.01)

(58) Field of Classification Search
CPC ....... C07C 29/149; C07C 29/40; C07C 67/08; C07C 31/202; B01J 23/72; B01J 21/02
See application file for complete search history.

(56) References Cited

U.S. PATENT DOCUMENTS

| | | | |
|---|---|---|---|
| 2,060,880 A | 11/1936 | Lazier | |
| 4,453,026 A | 6/1984 | Tahara et al. | |
| 5,030,771 A | 7/1991 | Fuhrmann et al. | |
| 6,448,457 B1 | 9/2002 | Hesse et al. | |
| 9,102,583 B2 * | 8/2015 | Yang | .................... C07C 29/149 |
| 2008/0207953 A1 | 8/2008 | Houssin et al. | |
| 2010/0179356 A1 | 7/2010 | Liu et al. | |
| 2018/0002303 A1 | 1/2018 | Duefert et al. | |

FOREIGN PATENT DOCUMENTS

| | | |
|---|---|---|
| CN | 101475443 A | 7/2009 |
| DE | 3843956 A1 | 6/1990 |
| DE | 19809418 A1 | 9/1999 |
| WO | WO-2007006719 A1 | 1/2007 |
| WO | WO-2016110520 A1 | 7/2016 |

OTHER PUBLICATIONS

European Search Report for EP Patent Application No. 15178919.5, dated Feb. 2, 2016.
Teunissen, T., et al., "Ruthenium catalysed hydrogenation of dimethyl oxalate to ethyleneglycol", Chemical communications, 1997, vol. 1, Issue 7, pp. 667-668.
Wang, Y., et al., "Remarkable enhancement of Cu catalyst activity in hydrogenation of dimethyl oxalate to ethylene glycol using gold", Catalysis Science & Technology, 2012, vol. 2, Issue 8, pp. 1637-1639.
Yue, H., et al., "Ethylene glycol: properties, synthesis, and applications", Chemical Society Reviews, 2012, vol. 41, Issue 11, pp. 4218-4244.
Zhuxia, et al., "Studies on Hydrogenation of Dimethyl Oxalate on Cu/SiO2 catalyst", Huaxue Fanying Gongcheng Yu Gongyi (Chemical Reaction Engineering and Technology), 2004, vol. 20, Issue 2, pp. 121-128.

(Continued)

*Primary Examiner* — Jafar Parsa
(74) *Attorney, Agent, or Firm* — Drinker Biddle & Reath LLP

(57) ABSTRACT

Process for preparing monoethylene glycol (MEG) by metal-catalyzed reaction of a dialkyl oxalate of the formula I

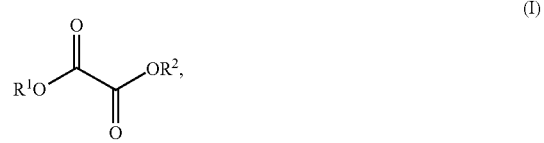

(I)

where $R^1$ and $R^2$ are each, independently of one another, methyl, ethyl, n-propyl or isopropyl, with hydrogen ($H_2$), wherein the dialkyl oxalate (I) is used as melt or as a solution in a solvent, dialkyl oxalate (I) and $H_2$ are used in a molar ratio of $H_2$:dialkyl oxalate (I) in the range from 4.0 to 30 and the reaction is carried out continuously in a reactor at a cross-sectional loading of ≥10 m/s, a temperature in the range from 150 to 270° C., a pressure in the range from 150 to 390 bar and in the presence of a chromium-free heterogeneous catalyst comprising copper.

17 Claims, No Drawings

(56) References Cited

OTHER PUBLICATIONS

International Search Report for PCT/EP2016/067706 dated Oct. 21, 2016.
Written Opinion of the International Searching Authority for PCT/EP2016/067706 dated Oct. 21, 2016.

* cited by examiner

METHOD FOR PRODUCING MONOETHYLENE GLYCOL

CROSS-REFERENCE TO RELATED APPLICATIONS

This application is a national stage application (under 35 U.S.C. § 371) of PCT/EP2016/067706, filed Jul. 26, 2016, which claims benefit of European Application No. 15178919.5, filed Jul. 29, 2015, both of which are incorporated herein by reference in their entirety.

The invention relates to a process for preparing monoethylene glycol.

Monoethylene glycol, formula HO—$CH_2$—$CH_2$—OH, will hereinafter be abbreviated to MEG or referred to as ethylene glycol for short.

Ethylene glycol is an important platform chemical which is used for the preparation of polyesters, as antifreeze, lubricant, plasticizer and much more. In 2010, the global production was about 20 million metric tons, with a projected annual growth of 5-10% per annum. The main production route is based on the aqueous hydrolysis of ethylene oxide to MEG, with ethylene oxide being obtained from petrochemical sources. A further important process is the hydrogenation of oxalates.

The preparation of MEG by hydrogenation of derivatives of oxalic acid (formula: HOOC—COOH) has been described a number of times. Apart from research work, the industrial processes carried out at present are also based on the hydrogenation of oxalic esters, usually dimethyl oxalate (DMO), over copper catalysts in the gas phase. The focus is on the hydrogenation by a process originally developed by Ube (U.S. Pat. No. 4,453,026 A, Ube Industries Ltd.) of dimethyl oxalate prepared by reaction of methanol and CO. In no document is it stated how MEG can be prepared proceeding from oxalates in high yield and with small amounts of interfering secondary components at high pressure.

C3 or C4 compounds, which can comprise, for example, 1,2-propanediol, 1,2-butanediol, butanal, propanal and also C2 molecules such as acetaldehyde, are undesirable in the output since they can be separated only with difficulty from the product, get in the pure product and can have an adverse effect on the color stability of the ethylene glycol or downstream products thereof. Dimethyl oxalate can also decompose into C1 molecules such as CO or $CO_2$, as a result of which the selectivity and profitability of the overall process is reduced.

L. Zhuxia et al., Huaxue fanying gongcheng yu gongyi (Chemical Reaction Engineering and Technology), 2004, 20, pages 121-128, describes the gas-phase reaction of DMO with hydrogen over $SiO_2$-supported copper catalysts at from 523 to 623 K (250 to 350° C.) and from 1.5 to 5.0 MPa (loc. cit. FIG. 5), corresponding to from 15 to 50 bar. The molar ratio of $H_2$/DMO was in the range from 25 to 160 (loc. cit. FIG. 4). It was found that a high pressure and a high molar ratio of $H_2$/DMO has a positive effect on the selectivity to MEG, but a low molar ratio of $H_2$/DMO leads to increased methyl glycolate formation. Simultaneous operation at a low molar ratio of $H_2$/DMO at high pressure was not examined, nor was the formation of interfering secondary components mentioned.

Y. Wang et al., Catal. Sci. Technol., 2012, 2, pages 1637-1639, mentions the formation of ethanol, 1,2-propanediol and 1,2-butanediol as undesirable secondary components in a gas-phase hydrogenation (loc. cit. page 1637, right-hand column, 3rd paragraph) of DMO to MEG at 453 K (180° C.). Nothing was said about the decomposition of DMO into CO or $CO_2$, and the hydrogenation also took place at a low pressure of 3.0 MPa (30 bar) and a high excess of $H_2$ ($H_2$/DMO=80:1) (loc. cit. table 1).

The metal-catalyzed liquid-phase hydrogenation of dialkyl esters of oxalic acid to form ethylene glycol at temperatures in the range from 200 to 275° C. is described in U.S. Pat. No. 2,060,880 (E. I. du Pont de Nemours & Comp.). In the case of diethyl oxide, a pressure in the range from 200 to 1000 atm (202.65 to 1013.25 bar) and a temperature in the range from 240 to 260° C. were examined (catalyst: copper chromite). Only above a high pressure of at least 600 atm (405.3 bar) is a virtually complete conversion of the diester achieved. The yield of MEG was 80-85% at 600 atm and 85% at 1000 atm. Only ethanol and ether are mentioned as possible by-products, and the process is also carried out batchwise.

The first publication DE 38 43 956 A1 (Hüls AG) reports a continuous high-pressure liquid-phase hydrogenation of dicarboxylic diesters to form alpha-omega diols over copper chromite catalysts. The reactions are carried out at from 120 to 220° C. and from 50 to 400 bar, with the yield in the case of, for example, 1,6-hexanediol being 93% at 300 bar. However, the preparation of MEG from oxalic diesters and secondary components associated therewith are not mentioned.

CN 101 475 443 A (China Petrochem. Corp.) reports the preparation of MEG from oxalates over copper catalysts in the intermediate pressure range from 0.1 to 10.0 MPa (1 to 100 bar) and in the temperature range from 120 to 300° C. The mode of operation was selected so as to achieve a long catalyst operating life and a short regeneration time. The use of higher pressures and their effect on the selectivity is not mentioned. The molar ratio of Hz/ester is stated to be in the range from 5 to 300. In the examples, the temperature is in the range from 180 to 270° C., the pressure is in the range from 0.8 to 4.0 MPa (8 to 40 bar) and the molar ratio of Hz/ester is in the range from 60 to 150. Despite the large excess of hydrogen, only a selectivity in the range from 81 to 96% could be achieved at full conversion in the examples reported.

H. Yue et al., Chem. Soc. Rev., 2012, 41, pages 4218-4244, refers to the homogenously and heterogeneously metal-catalyzed hydrogenation of DMO.

For the batchwise hydrogenation in the liquid phase, it is said that a high pressure of, for example, 200 bar is necessary for an efficient reaction under homogeneous catalysis (page 4223, right-hand column). Although the formation of secondary components by esterification, transesterification and decarboxylation reactions is mentioned, possible secondary components are not described in detail. Specific homogeneous Ru catalysts allow the preparation of MEG from DMO even under mild conditions of 80-100 bar of $H_2$ and 120° C. Furthermore, results for the continuous hydrogenation of DMO in the gas phase over heterogeneous copper catalysts are cited (pages 4224-4225). MEG yields of up to 99% are achieved at a molar ratio of $H_2$/DMO in the range from 50 to 200, from 463 to 516 K (190 to 243° C.) and from 20 to 30 bar.

H. T. Teunissen et al., Chem. Commun., 1997, pages 667-668, describes the batchwise homogeneous hydrogenation of DMO to MEG under mild conditions (70 bar of $H_2$, 100° C.) over ruthenium catalysts. The yields are only in the case of selected Ru catalysts having particular ligands up to 95%.

US 2010/0179356 A1 (J. Liu et al.) relates to the preparation of ethylene glycol by hydrogenation of oxalate(s) in the gas phase at a pressure in the range from 2 to 100 bar, comprising a) a first reaction zone having a first copper-comprising catalyst and b) a second reaction zone having a second copper-comprising catalyst.

It was an object of the present invention to overcome disadvantages of the prior art and provide an improved economical process for preparing MEG, in which the MEG is obtained in high yield, in particular space-time yield, and purity. The process should be able to be carried out at a high conversion, in particular also in a continuous mode of operation, and have a high selectivity, i.e., for example, a very low degree of decomposition of the starting materials and a very small formation of secondary components, including potentially color-imparting secondary components. The catalyst used should have a long life (operating life) under the process conditions. The preparative process should additionally be particularly simple and economical.

We have accordingly found a process for preparing monoethylene glycol (MEG) by metal-catalyzed reaction of a dialkyl oxalate of the formula I

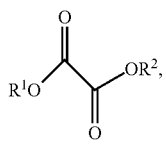

(I)

where $R^1$ and $R^2$ are each, independently of one another, methyl, ethyl, n-propyl or isopropyl, with hydrogen ($H_2$), wherein the dialkyl oxalate (I) is used as melt or as a solution in a solvent, dialkyl oxalate (I) and $H_2$ are used in a molar ratio of $H_2$:dialkyl oxalate (I) in the range from 4.0 to 30 and the reaction is carried out continuously in a reactor at a cross-sectional loading of ≥10 m/s, a temperature in the range from 150 to 270° C., a pressure in the range from 150 to 390 bar and in the presence of a chromium-free heterogeneous catalyst comprising copper.

The chemical reaction corresponds to the following reaction equation:

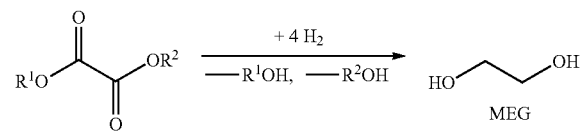

The radicals $R^1$ and $R^2$ are each, independently of one another, methyl, ethyl, n-propyl or isopropyl.

For example, $R^1=R^2$=ethyl. Particular preference is given to $R^1=R^2$=methyl, so that the starting material to be hydrogenated is dimethyl oxalate (DMO).

According to the invention, it has been recognized that a high conversion of ester (I) of in particular ≥90% can be realized with low decomposition of the ester (I) of in particular <10% and high selectivity to ethylene glycol by means of the process according to the claims.

The selectivity (defined as described below in the examples) to ethylene glycol, based on dialkyl oxalate I used, is in particular above 90%, more particularly above 95%, very particularly ≥96%, over the entire operating life of the hydrogenation catalyst.

In addition, the liquid-phase process has been found to be advantageous compared to the gas-phase processes of the prior art, since, in particular, advantages in terms of energy and process engineering are achieved (no vaporization step for the starting material, no condensation step for the reactor output).

The oxalic ester I can be used as a solution in a solvent. For this purpose, the oxalic ester I can be introduced as solid into the desired solvent. This is advantageous when the prior production of oxalic ester I has formed by-products which can have an inhibiting or damaging effect on the hydrogenation process or are converted by hydrogenation into compounds which, owing to their physical properties, cannot be separated, or be separated only with difficulty, from ethylene glycol and can be removed as solid by intermediate isolation of oxalic ester I, e.g. DMO.

As an alternative, the oxalic ester I can also be introduced as gaseous stream into a desired solvent. This is advantageous, for example, when coproduction of oxalic ester I, e.g. DMO, and MEG in two plants connected in series for the preparation of oxalic ester I, e.g. DMO, and direct further processing to form MEG is sought and a variable proportion of oxalic ester I, e.g. DMO, is to be discharged.

The oxalic ester I can also be used as pure melt or a melt admixed with small amounts, e.g. from 0.1 to 10% by weight, of solvent(s) in the process of the invention. In this way, the amount of solvent(s) in the process can be minimized, which can have a positive effect on a final isolation of the MEG since the circulating streams of solvent(s) are made considerably smaller in this way.

Examples of solvent which can be used, and are inert under the reaction conditions, are aliphatic or aromatic alcohols, hydrocarbons, ether based on ethylene oxide and/or propylene oxide, aliphatic or aromatic esters or carbonates, water, substituted phenol derivatives. It is also possible to use mixtures of two or more solvents, should this be desired. Preferred solvents are methanol, ethanol, n-propanol, isopropanol and/or ethylene glycol. Methanol and ethylene glycol are particularly preferred.

In a particular embodiment, the oxalic ester I is fed in as melt, with mixing of the starting material I with a crude product substream (liquid recycle at the reactor) leading to a solution of the starting material I, e.g. DMO in MEG/MeOH, as feed to the reactor.

The reaction is carried out at a temperature in the range from 150 to 270° C., preferably from 170 to 260° C., more particularly at a temperature in the range from 180 to 250° C., very particularly at a temperature in the range from 190 to 240° C.

The reaction is carried out at a pressure in the range from 150 to 390 bar, preferably at a pressure in the range from 160 to 290 bar, more particularly at a pressure in the range from 180 to 270 bar.

In the process of the invention, dialkyl oxalate (I) and $H_2$ are preferably used in a molar ratio of $H_2$:dialkyl oxalate (I) in the range from 4.2 to 20, in particular in the range from 4.3 to 15. The molar ratio of $H_2$:dialkyl oxalate (I) is the molar ratio of fresh hydrogen to fresh dialkyl oxalate (I), i.e. of the two starting materials which are introduced continuously for the reaction. If an after-reactor is used, it is also possible for the main reactor to be operated with substoichiometric amounts of hydrogen.

The reaction is carried out continuously in a reactor at a cross-sectional loading (Q) of ≥10 m/s. The cross-sectional loading (=volume flow density) Q is defined as follows:

$$Q = \frac{\dot{v}}{A} = \frac{\text{Volume thoughput}}{\text{Cross} - \text{sectional area of the reactor}}$$

The unit of Q is m/s.

The reaction is carried out continuously in a reactor at a preferred cross-sectional loading (Q) in the range from ≥10 to 1000 m/s, more preferably in the range from >10 to 500 m/s, more particularly in the range from 15 to 400 m/s, very particularly in the range from 20 to 300 m/s.

The continuous reaction according to the invention is preferably carried out at a space velocity over the catalyst in the range from 0.01 to 5.0 kg of dialkyl oxalate (I)·$\text{liter}_{cat.}^{-1}\cdot\text{h}^{-1}$, particularly preferably at a space velocity over the catalyst in the range from 0.1 to 2.0 kg of dialkyl oxalate (I)·$\text{liter}_{cat.}^{-1}\cdot\text{h}^{-1}$, more particularly preferably at a space velocity over the catalyst in the range from 0.2 to 1.5 kg of dialkyl oxalate (I)·$\text{liter}_{cat.}^{-1}\cdot\text{h}^{-1}$.

In a preferred embodiment of the process of the invention, the space velocity over the catalyst is set so that the conversion of dialkyl oxalate (I) is ≥90%, preferably ≥95%, particularly preferably ≥96%.

Reactors used for the reaction according to the invention (hydrogenation of the oxalic ester I) are types known to those skilled in the art. Examples are shaft reactors, in particular tube reactors, and shell-end-tube reactors, etc. The hydrogenation can be carried out in one reactor or in a plurality of reactors arranged in parallel or in series, including a number of types of reactor combined with one another.

The hydrogenation is preferably operated at partial conversion in a first reactor with liquid recycle and after-reactor. For this purpose, the crude product is, in the case of one or more reactors arranged in series or in parallel, recirculated between the reactors or after the reactors by means of a pump into a reactor located further upstream in the process, with the recycle stream preferably being used for removing the heat of reaction in the recycle by means of a heat exchanger. The hydrogen consumed by the hydrogenation and losses via offgas is correspondingly replaced. The weight ratio of recycle to output is in particular 1-100:1, preferably 3-50:1, particularly preferably 5-20:1, e.g. 10:1.

Preference is given to the reaction being carried out continuously in a reactor and the reactor being operated with a recycle by recirculating part of the reactor output from the reactor output to the reactor inlet.

If a combination of main reactor and after-reactor is used, preference is given to recirculating a recycle gas stream downstream of the main reactor and operating the after-hydrogenation using fresh hydrogen. As an alternative, the hydrogenation can be carried out without a recycle gas stream, with fresh gas being able to be newly fed in between individual reactors. An additional intermediate introduction of hydrogen in the reactor is likewise possible.

In the case of processes which operate for a relatively long time in order to produce industrial amounts of ethylene glycol product, a purge is preferably carried out to avoid accumulation of undesirable secondary components. Preference is therefore given to working up this purge stream further, e.g. in a further distillation apparatus.

Possible decomposition products of oxalic esters I, namely CO and $CO_2$, can likewise accumulate, for which reason part of the recycle gas stream is in this case preferably discharged in order to avoid an increase in concentration of decomposition products.

The process of the invention is carried out in the presence of a chromium-free heterogeneous catalyst comprising copper.

A chromium-free heterogeneous catalyst is to be understood as one in which no chromium (Cr) in any oxidation state is added in the production of the catalyst. As a result of the production method or due to impurities in the catalyst starting materials, the catalyst should comprise less than 0.5% by weight, preferably less than 0.1% by weight, particularly preferably less than 0.01% by weight, of chromium in any oxidation state.

The catalysts utilized for the hydrogenation comprise, as active component, at least Cu; in addition, one or more elements selected from the group consisting of Ru, Re, Co, La, Mo, W, Ti and Zr can be comprised as further hydrogenation metals. Preference is given to, for example, a mixture of Cu and an oxide of a further element selected from the group consisting of La, Mo, W, Ti and Zr. In the case of such a mixture of copper and a metal oxide, the use of lanthanum is particularly preferred.

The % by weight of the hydrogenation metal or hydrogenation metals (calculated as element(s)), e.g. copper, based on the total weight of the catalyst is preferably in the range from 0.5 to 85, more preferably in the range from 10 to 80, more particularly preferably in the range from 25 to 65.

The % by weight of the oxide from the group consisting of La, Mo, W, Ti and Zr, e.g. of lanthanum oxide ($La_2O_3$), based on the total weight of the catalyst is preferably in the range from 0.01 to 30, more preferably in the range from 0.5 to 20, more particularly preferably in the range from 3 to 15.

The hydrogenation metal(s) is/are preferably applied to a support system. Suitable supports comprise oxides or consist of oxides based on B, Al, Si, Ti, Zr, La, Ce or Cr, e.g. aluminum oxide or zirconium dioxide, or carbon, for example in the form of activated carbon. A further support which is nonoxidic is, for example, SiC.

The % by weight of the support material, e.g. of the aluminum oxide, based on the total weight of the catalyst is in particular in the range from 15 to 98, more particularly in the range from 19.5 to 89.5, very particularly in the range from 32 to 72.

In a preferred example, the catalyst comprises, based on total weight of the catalyst, from 10 to 80% by weight, in particular from 25 to 65% by weight, of copper, from 0.5 to 20% by weight, in particular from 3 to 15% by weight, of lanthanum oxide and from 19.5 to 89.5% by weight, in particular from 32 to 72% by weight, of aluminum oxide.

The production of the catalysts is, for example, effected by impregnation of the appropriate support with activated metal precursors, for example corresponding metal salt solutions, e.g. a Cu salt solution. Precipitated catalysts in which the active components are precipitated onto a support or are precipitated together with the support material from dissolved precursors thereof are also suitable. After drying and optionally calcination of the catalyst material, the catalyst is preferably activated by means of hydrogen before commencement of the hydrogenation. The catalysts are generally shaped bodies having an average size of more than one millimeter. Preference is given to using extrudates, pellets, star extrudates, trilobes, hollow bodies, etc. The bulk density of the catalyst is in particular in the range from 0.5 to 2.0 g/ml.

In a particular embodiment of the process of the invention, the hydrogenation of the oxalic ester I is carried out by means of a shaped catalyst body whose precursor can be produced by a process in which (i) an oxidic material comprising copper oxide, aluminum oxide and lanthanum oxide is provided, (ii) pulverulent metallic copper and/or copper flakes and optionally graphite are added to the oxidic material, (iii) the mixture resulting from ii is shaped to give a shaped body, where the oxidic material is obtainable by simultaneous or sequential precipitation of the component copper oxide, the component aluminum oxide and the component lanthanum oxide and subsequent drying and calcination and the shaped catalyst body is calcined again after shaping in step iii.

In the shaped catalyst bodies, which are also described in more detail below, the oxidic material more particularly comprises (a) copper oxide in a proportion in the range of $50 \leq x \leq 80\%$ by weight, preferably $55 \leq x \leq 75\%$ by weight, in each case calculated as CuO, (b) aluminum oxide in a proportion in the range of $15 \leq y \leq 35\%$ by weight, preferably $20 \leq y \leq 30\%$ by weight, and (c) lanthanum oxide in a proportion in the range of $2 \leq z \leq 20\%$ by weight, preferably $3 \leq z \leq 15\%$ by weight, more preferably $3.5 \leq z \leq 10\%$ by weight, in each case based on the total weight of the oxidic material after calcination, where: $80 \leq x+y+z \leq 100$, in particular $95 \leq x+y+z \leq 100$.

In the case of this catalyst for the hydrogenation, the component copper oxide, the component aluminum oxide and the component lanthanum oxide are precipitated simultaneously or in succession, preferably by means of a sodium carbonate solution, subsequently dried, calcined, shaped, e.g. tableted, and calcined again.

Copper oxide is CuO, $Cu_2O$ or a mixture of the two oxides. In the specification of amounts, copper(I) oxide is calculated as copper(II) oxide.

Aluminum oxide is $Al_2O_3$ and lanthanum oxide is $La_2O_3$.

A particularly useful precipitation method is the following:

A) A copper salt solution, an aluminum salt solution and a solution of a salt of lanthanum or a solution comprising copper salt, aluminum salt and lanthanum salt are precipitated simultaneously or in succession by means of a sodium carbonate solution.

B) Precipitation of a copper salt solution and, separately, a solution of a salt of lanthanum or a solution comprising copper salt and a salt of lanthanum on a prefabricated aluminum oxide support. The latter is, in a particularly preferred embodiment, present as powder in an aqueous suspension. However, the support material can also be present as, for example, spheres, extrudates, crushed material or pellets.

In a particular embodiment of B), namely (B1), a copper salt solution and a solution of a salt of lanthanum or a solution comprising copper salt and a salt of lanthanum are precipitated, preferably by means of sodium carbonate solution. An aqueous suspension of the support material aluminum oxide is used as substrate.

Precipitates resulting from A) or B) are separated off in a conventional manner, e.g. filtered off, and preferably washed free of alkali, as is described, for example, in DE 198 09 418 A1 (BASF AG).

After precipitation of the components, in particular the end products from A) or from B), these are dried at elevated temperature, in particular at temperatures from 50 to 150° C., preferably at from 110 to 130° C., (e.g. for a period of from 5 to 30 hours, preferably from 10 to 20 hours), and then preferably calcined, for example at generally from 200 to 700° C., in particular from 400 to 650° C., for a period of from 0.5 to 6 hours, in particular from 1 to 3 hours.

As starting materials for A) and/or B), it is in principle possible to use all Cu(I) and/or Cu(II) salts which are soluble in the solvents used for the precipitation (with preference being given to water), for example nitrates, carbonates, acetates, oxalates or ammonium complexes, and also analogous aluminum salts and salts of lanthanum. Particular preference is given to using copper(II) nitrate as copper salt. As lanthanum salt, preference is given to using lanthanum nitrate. As aluminum salt, preference is given to using aluminum nitrate.

The composition of the oxidic material is preferably such that the proportion of copper oxide is in the range from 50 to 80% by weight, in particular from 55 to 75% by weight, in each case calculated as Cu©, the proportion of lanthanum oxide is in the range from 2 to 20% by weight, in particular from 3 to 15% by weight, and the proportion of aluminum oxide is in the range from 15 to 35% by weight, in particular from 20 to 30% by weight, in each case, for all components, based on the total weight of the sum of the abovementioned oxidic constituents, where these three oxides together make up at least 80% by weight, in particular at least 95% by weight, of the oxidic material after calcination, with any added cement, e.g. alumina cement, not being included as part of the oxidic material in the above sense.

In a preferred embodiment, the oxidic material comprises (a) copper oxide in a proportion in the range of $50 \leq x \leq 80\%$ by weight, preferably $55 \leq x \leq 75\%$ by weight, in each case calculated as CuO, (b) aluminum oxide in a proportion in the range of $15 \leq y \leq 35\%$ by weight, preferably $20 \leq y \leq 30\%$ by weight, and (c) lanthanum oxide in a proportion in the range of $2 \leq z \leq 20\%$ by weight, preferably $3 \leq z \leq 15\%$ by weight, more preferably $3.5 \leq z \leq 10\%$ by weight, in each case based on the total weight of the oxidic material after calcination, where: $80 \leq x+y+z \leq 100$, in particular $95 \leq x+y+z \leq 100$.

In the case of these catalysts used in the process of the invention, the addition of the lanthanum salt in the precipitation also leads to a high stability of the shaped body which ultimately results and is used as catalyst.

Pulverulent copper and/or copper flakes and optionally graphite is/are subsequently added to the oxidic material (step ii). Preference is given to adding pulverulent copper and graphite. The addition of graphite can also be carried out before the addition of copper; in this case, a precompaction is preferably firstly carried out. For example, graphite is added in amounts in the range from 0 to 5% by weight, preferably in the range from 0.5 to 4% by weight, particularly preferably in the range from 0.8 to 2% by weight, in each case based on the total weight of the oxidic material after calcination.

As pulverulent copper, preference is given to using pulverulent copper having a particle diameter in the range from 1 to 700 μm, preferably in the range from 5 to 500 μm. Particular preference is given to using a pulverulent copper for which sieve analysis gives a proportion of particles >500 μm of ≤6%, in particular a proportion of particles ≥350 μm of ≤5%. The particle morphology is preferably spherical.

As copper flakes, preference is given to using copper flakes which have a D 50 in the range from 5 to 40 μm, in particular in the range from 10 to 35 μm ("D 50" means that 50% of the particles are smaller than the value indicated). The sieve analysis preferably gives a proportion of particles >45 μm of ≤6%, particularly ≤2%. The copper flakes preferably have a lamellar flake structure.

Pulverulent copper and/or copper flakes together are preferably added in amounts in the range from 0.5 to 40% by weight, preferably in the range from 2 to 20% by weight, particularly preferably in the range from 3 to 10% by weight, in each case based on the total weight of the oxidic material after calcination.

In particular embodiments, the oxidic material can comprise at least one further component selected from the group consisting of oxides of the elements Re, Fe, Ru, Co, Rh, Ir, Ni, Pd and Pt in a proportion of not more than 10% by weight, preferably not more than 5% by weight, based on the total weight of the oxidic material after calcination.

In step iii, the mixture resulting from step ii is shaped to give a shaped body and then calcined. Graphite is preferably added to the mixture before shaping to give the shaped body. Graphite is preferably added in such an amount that shaping to give a shaped body can be carried out more readily. In a preferred embodiment, from 0.5 to 5% by weight, in particular from 1 to 3% by weight, of graphite, based on the total weight of the mixture resulting from step ii, is added.

The sum of the proportions of oxidic material, metallic copper powder and/or copper flakes and optionally graphite preferably makes up at least 95% by weight, in particular at least 98% by weight, of the shaped catalyst body.

The shaping in step iii preferably leads to pellets, rings, annular pellets, extrudates, honeycomb bodies or similar shaped bodies. All methods known from the prior art are suitable for this purpose.

After shaping, the shaped bodies obtained are calcined again, at least once. The calcination is in each case preferably carried out for a period of generally from 0.5 to 10 hours (h), in particular from 0.5 to 2.5 hours. The temperature in this at least one calcination step (and also in the optional repeated calcination steps) is generally in the range from 200 to 600° C., preferably in the range from 250 to 500° C. and particularly preferably in the range from 270 to 400° C.

In a further embodiment, the shaped body obtained can also be additionally treated with boiling water and/or steam before it is used for the hydrogenation.

When used as catalyst in the oxidic form, the shaped body is prereduced by means of reducing gases, for example hydrogen, preferably hydrogen/inert gas mixtures, in particular hydrogen/nitrogen mixtures, at elevated temperatures, e.g. in the range from 100 to 500° C., preferably in the range from 150 to 350° C. and in particular in the range from 180 to 200° C., before being supplied with the starting materials. Preference is given here to using a gas mixture having a proportion of hydrogen in the range from 1 to 100% by volume, particularly preferably in the range from 1 to 50% by volume.

In a preferred embodiment, the shaped body is activated in a manner known per se by treatment with reducing media before being used as catalyst. Activation is carried out either beforehand in a reduction oven or after installation in the reactor. If the reactor has been activated beforehand in a reduction oven, it is installed in the reactor and supplied directly under hydrogen pressure with the starting material(s).

After a catalytic preparation of MEG, the catalyst is separated off from the crude product in order to isolate the pure process product MEG. Many liquid-phase hydrogenations of oxalic esters use homogeneous catalysts which may have to be removed from the crude product by means of an additional distillation, reaction or extraction step. In the present process, heterogeneous catalysts are used, and in the case of these separation from the crude product is readily possible. Separation of the catalyst from the reaction solution takes place automatically in the preferred mode of operation in a fixed-bed reactor by retention of the catalyst in the reactor. Any catalyst particles which arise by abrasion of the catalyst can subsequently be additionally removed by means of a mesh, a gauze, a frit or techniques known to those skilled in the art.

The hydrogenation output which has been freed of the catalyst is preferably purified further. It comprises predominantly the hydrogenation product ethylene glycol and the alcohols $R^1OH$, $R^2OH$, and also, for the example of DMO as starting material I below, in small amounts, in each case based on the product ethylene glycol, less than 7 mol %, preferably less than 5 mol %, of 2-methoxyethanol, less than 2 mol %, preferably less than 1 mol %, of methyl glycolate, less than 5 mol %, preferably less than 2 mol %, of ethanol, and also possibly further products, usually in amounts of less than 1 mol %, preferably less than 0.5 mol %, in each case based on ethylene glycol, such as 1,2-propanediol, 1,2-butanol, 2,3-butanol, acetaldehyde, 1,2-dimethoxyethane, 1,1-dimethoxyethane, 2,2-dimethoxypropane, dimethyl ether, methyl acetate, esters of formic acid and possibly other compounds in insignificant amounts.

Preferred embodiments of the purification of MEG are described in more detail below for the example of DMO being used.

The crude hydrogenation product is preferably freed of methanol, methyl glycolate and other impurities by removal of relatively low boilers and relatively high boilers from the MEG by distillation. The purification of MEG is preferably carried out in two, in particular at least three, distillation columns.

The hydrogenation output is freed of high boilers (components having boiling points higher than MEG) in a first column, with MeOH, ethanol, which may additionally contain acetaldehyde, dimethoxyethane and other low boilers, being obtained at the top. The stream is fed into the enrichment section of the column, and the pressure is preferably in the range from 0.5 to 4 bar, preferably from 1 to 3 bar, particularly preferably from 1 to 2.5 bar. The temperature is preferably 25-300° C., preferably 60-250° C. The overhead stream, which consists mainly of methanol, can subsequently be separated separately and the methanol can be recycled, if desired, either by recirculation into the process or in a synthesis reactor for preparing dimethyl oxalate operated in conjunction. The bottom product, which comprises mainly MEG and further by-products such as methyl glycolate or ethanol, is introduced into a further column which is preferably operated at a lower pressure than the first column. Here, methyl glycolate and also ethanol and impurities comprised therein are separated off at the top and, in the case of the recycled mode of operation of the reactor, preferably recirculated with the recycle to the reactor. The pressure in the second column is in the range from 0.05 to 1 bar, preferably from 0.1 to 0.8 bar, particularly preferably from 0.1 to 0.5 bar. The temperature is 25-250° C., preferably 60-200° C. The bottom product, consisting mainly of MEG and high boilers (components having boiling points higher than MEG), e.g. 1,2-butanediol, is freed of high-boiling impurities, which are discharged at the bottom, in the third column. The pressure in the third column is in the range from 10 to 800 mbar, preferably from 25 to 500 mbar, particularly preferably from 55 to 350 mbar. The temperature is 25-250° C., preferably 80-200° C. After the third column, the MEG has a purity of 99.9% by weight. If this cannot be ensured, further separation stages, e.g. one or more distillation columns, can follow.

The columns can have various internals such as random packing elements, sheet metal packing, mesh packing or trays.

Alternative purification concepts comprise, for example, removal of the impurities by means of membrane filtration. The removal of traces of water by means of concentrated sodium hydroxide solution or of potassium hydroxide solution is likewise possible. After these water removal methods, the MEG is preferably purified further in at least one column.

The bed volume of the catalyst (liter$_{cat.}$) was determined by means of a graduated 250 ml measuring cylinder (not conical, internal diameter 37 mm).

The bulk density of the catalyst was determined by introducing 100 ml of a catalyst into a 250 ml measuring cylinder (not conical, internal diameter 37 mm). The mass of the catalyst introduced was determined by difference weighing of the measuring cylinder with and without catalyst on a balance having a loading of up to 4000 g and a reading precision of 0.01 g. The bulk density of the catalyst could be determined from the mass and the volume (bulk density [kg/l]=weight [g]/volume [ml]).

All pressures reported are absolute pressures.

EXAMPLES

The analysis of all secondary components was carried out via GC percent by area [% by area]. The proportion of methyl glycolate and DMO was additionally measured in GC percent by weight. The gas-chromatographic separation was carried out over a solid phase (Stabil-WAX, 60 m, O=320 μm) using hydrogen as carrier gas (flow: 1.1 ml/min.) and an FID.

The selectivity of the catalysts under the reaction conditions was determined according to the formula $$\text{Selectivity}[\%] = \frac{\text{Proportion }(MEG)}{\text{Proportion }(\text{EtOH, 2-OMe-EtOH,}} \cdot 100$$
$$\text{1,2-propanediol, 1,2-butanediol, }MEG)$$

where the proportion is expressed in percent by area from the GC analysis. The proportions of the possible products in the denominator were summed. (EtOH=ethanol; 2-OMe-EtOH=2-methoxyethanol).

The conversion of the DMO is given by the formula $$\text{Conversion of } DMO \ [\%] = \left(1 - \frac{\% \text{ by weight }(DMO)_{output}}{\% \text{ by weight }(DMO)_{feed}}\right) \cdot 100$$

The partial reduction in the output is defined according to the formula

Partial reduction [%] =

$$\frac{\% \text{ by weight (Me glycolate)}}{M(\text{Me glycolate})} \cdot \frac{M(DMO)}{\% \text{ by weight }(DMO)_{feed}} \cdot 100$$

(M=molar mass; Me glycolate=methyl glycolate=methyl ester of glycolic acid=HO—CH$_2$—CO(O)—OCH$_3$).

Comparative Example 1 at Low Pressure

The apparatus used consisted of a feed section with reservoir and pump, a 77 cm long tube reactor having an internal diameter of 1.4 cm and external double-wall oil heating or cooling which was operated in the down flow mode, a separator cooled to 6° C. and also fresh gas and offgas facilities. The molar ratio of fresh hydrogen to DMO was 16:1, with the excess gas being discharged as offgas. The reactor was operated in the single pass mode.

The reactor was filled with 10 ml of a barium-doped copper chromite (3 mm pellets). The catalyst bed volume of 100 g of catalyst was 81 ml. The catalyst is a commercial product of BASF SE having the designation "Cu 1155 T" (≤69% by weight of chromium(III) oxide, ≤21% by weight of copper oxide, ≤10% by weight of barium oxide). Steatite balls were introduced as inert bed above and below the catalyst. After making inert by means of nitrogen, the catalyst was activated using a nitrogen/hydrogen mixture at atmospheric pressure. After activation of the catalyst, a solution having the composition 9% by weight of DMO, 45% by weight of methanol (MeOH) and 46% by weight of MEG was introduced as reactor feed.

At a space velocity over the catalyst of 0.23 kg of DMO·liter$_{cat.}^{-1}$·h$^{-1}$, 78% of the DMO was reacted (liter$_{cat.}$=catalyst bed volume). At a selectivity of not more than 10%, 2-methoxyethanol, dimethyl ether, methyl formate and methyl glycolate were found as further components in addition to MEG as main product. An offgas measurement indicated that the major part of the DMO reacted (at least 85% by weight based on DMO reacted) was to be found in the form of CO and CO$_2$ in the offgas.

Comparative Example 2a

The apparatus used consisted of a feed section with reservoir and pump, a 1.80 m long tube reactor having an internal diameter of 3.4 cm and external double-wall oil heating or cooling which was operated in the down flow mode, a water-cooled first separator, a second separator cooled to 6° C., a circulation pump and also fresh gas and offgas facilities. The molar ratio of fresh hydrogen to DMO was 13:1, with the excess gas being discharged as offgas. The weight ratio of recycle to feed was about 11-22:1.

The reactor was filled with 50 ml of a CuO (67% by weight)/La$_2$O$_3$ (5% by weight)/Al$_2$O$_3$ catalyst (3 mm pellets). The catalyst bed volume of 100 g of catalyst was 62 ml. The catalyst was produced in a manner analogous to WO 2007/006719 A1 (BASF AG), pages 13-14, example 1. At the entrance to the reactor, 15 ml glass spheres were introduced as inert bed above the catalyst. After making inert by means of nitrogen, the catalyst was activated using a nitrogen/hydrogen mixture at atmospheric pressure. After activation of the catalyst, the circulation was taken into operation using a solution of ethylene glycol (10% by weight) in methanol and the target pressure in the reactor and also the target temperature was set. 25% by weight of DMO in MeOH were introduced as feed.

The liquid reaction outputs obtained in the separators were collected and combined and analyzed.

| Input | 1 | 2 | 3 | 4 | 5 |
|---|---|---|---|---|---|
| Pressure [bar] | 170 | 170 | 170 | 170 | 170 |
| Temperature [° C.] | 170 | 190 | 210 | 210 | 230 |
| Throughput [kg$_{DMO}$ · liter$_{cat.}^{-1}$ · h$^{-1}$] | 0.20 | 0.20 | 0.20 | 0.10 | 0.10 |
| Recycle/feed [g/g] | 16 | 15 | 11 | 21 | 22 |
| Cross-sectional loading [m/s] | 1.9 | 1.7 | 1.3 | 1.2 | 1.3 |
| H$_2$/DMO [mol/mol] | 13 | 13 | 13 | 26 | 26 |
| Conversion of DMO [molar] | 34 | 44 | 65 | 92 | 100 |
| Partial reduction (methyl glycolate) [molar] | 19 | 13 | 7 | 6 | <1 |

-continued

| Input | 1 | 2 | 3 | 4 | 5 |
|---|---|---|---|---|---|
| Selectivity to MEG [%] | 84 | 88 | 95 | 97 | 81 |
| Decomposition of DMO [%] | 9 | 16 | 29 | 32 | 17 |
| 1,2-BDO [% by area] | <0.001 | <0.001 | <0.001 | <0.001 | 0.33 |
| 1,2-PDO [% by area] | <0.001 | <0.001 | 0.003 | 0.01 | 0.8 |
| EtOH [% by area] | <0.001 | 0.05 | 0.06 | 0.12 | 1.62 |
| 2-OMe—EtOH [% by area] | 0.1 | 0.2 | 0.6 | 0.9 | 0.9 |

(BDO=Butanediol, PDO=Propanediol).

Comparative Example 2b

Example 2a was repeated at higher pressure; in addition, a higher level of recycle was employed.

| Input | 1 | 2 | 3 | 4 | 5 |
|---|---|---|---|---|---|
| Pressure [bar] | 200 | 200 | 200 | 200 | 200 |
| Temperature [° C.] | 200 | 215 | 230 | 215 | 230 |
| Throughput [$kg_{DMO} \cdot liter_{cat.}^{-1} \cdot h^{-1}$] | 0.20 | 0.20 | 0.20 | 0.15 | 0.15 |
| Recycle/feed [g/g] | 38 | 35 | 28 | 40 | 33 |
| Cross-sectional loading [m/s] | 4.3 | 4.0 | 3.2 | 3.4 | 2.8 |
| $H_2$/DMO [mol/mol] | 13 | 13 | 13 | 17 | 17 |
| Conversion of DMO [molar] | 99 | 99 | 100 | 100 | 100 |
| Partial reduction (methyl glycolate) [molar] | 4 | 3 | 1 | 2 | 1 |
| Selectivity to MEG [%] | 96 | 91 | 80 | 87 | 77 |
| Decomposition of DMO [%] | 49 | 42 | 28 | 30 | 18 |
| 1,2-BDO [% by area] | 0.002 | 0.006 | 0.03 | 0.01 | 0.04 |
| 1,2-PDO [% by area] | 0.02 | 0.07 | 0.43 | 0.20 | 0.51 |
| EtOH [% by area] | 0.11 | 0.27 | 0.83 | 0.58 | 1.12 |
| 2-OMe—EtOH [% by area] | 0.14 | 0.30 | 0.51 | 0.36 | 0.55 |

Example 3 According to the Invention

The apparatus used consisted of a feed section with reservoir and pump, with a 4 m long coil tube reactor having an internal diameter of 0.4 cm, which was operated isothermally in the down flow mode, a separator, a circulation pump and also fresh gas and offgas facilities. The molar ratio of fresh hydrogen to DMO was 10:1, with the excess gas being discharged as offgas. The mass ratio of recycle to feed was 10:1.

The reactor was filled with 75 g of a CuO (67% by weight)/$La_2O_3$ (5% by weight)/$Al_2O_3$ catalyst (3 mm pellets), the same catalyst as in examples 2, and inert material (3 mm glass spheres), likewise as in examples 2. After making inert by means of nitrogen, the catalyst was activated using a nitrogen/hydrogen mixture at atmospheric pressure. After activation of the catalyst, the circulation was taken into operation using a solution of ethylene glycol (10% by weight) in methanol and the target pressure in the reactor and also the target temperature was set. 15% by weight of DMO in MeOH were introduced as feed.

The liquid reaction outputs obtained in the separators were collected and combined and analyzed. The offgas was examined spectroscopically by means of online analysis to determine its CO and $CO_2$ content.

| Input | 1 | 2 | 3 | 4 |
|---|---|---|---|---|
| Pressure [bar] | 250 | 250 | 250 | 250 |
| Temperature [° C.] | 210 | 220 | 220 | 230 |
| Throughput [$kg_{DMO} \cdot liter_{cat.}^{-1} \cdot h^{-1}$] | 0.32 | 0.31 | 0.64 | 0.74 |
| Recycle/feed [g/g] | 10 | 10 | 10 | 10 |
| Cross-sectional loading [m/s] | 109 | 109 | 219 | 255 |
| $H_2$/DMO [mol/mol] | 10 | 10 | 10 | 10 |
| Conversion of DMO [molar] | 92 | 99 | 98 | 97 |
| Partial reduction (methyl glycolate) [molar] | 5 | 9 | 16 | 22 |
| Selectivity to MEG [%] | 96 | 96 | 97 | 96 |
| Space-time yield [$kg_{MEG} \cdot litercat^{-1} \cdot h^{-1}$] | 0.13 | 0.15 | 0.31 | 0.31 |
| Decomposition of DMO [%] | 6 | 7 | 5 | 7 |
| 1,2-BDO [% by area] | 0.005 | <0.001 | <0.001 | <0.001 |
| 1,2-PDO [% by area] | 0.012 | 0.015 | <0.001 | <0.001 |
| EtOH [% by area] | 0.12 | 0.19 | 0.12 | 0.09 |
| 2-OMe—EtOH [% by area] | 0.04 | 0.06 | 0.07 | 0.07 |

The crude output was, at incomplete conversion, subsequently conveyed through an after-reactor in order to achieve complete conversion. The selectivities here were identical to the reaction in the main reactor.

The invention claimed is:

1. A process for preparing monoethylene glycol (MEG) by metal-catalyzed reaction of a dialkyl oxalate of the formula I

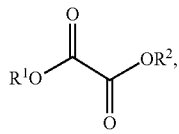

(I)

where $R^1$ and $R^2$ are each, independently of one another, methyl, ethyl, n-propyl or isopropyl, with hydrogen ($H_2$), wherein the dialkyl oxalate (I) is used as melt or as a solution in a solvent, dialkyl oxalate (I) and $H_2$ are used in a molar ratio of $H_2$:dialkyl oxalate (I) in the range from 4.0 to 30 and the reaction is carried out continuously in a reactor at a cross-sectional loading of ≥10 m/s, a temperature in the range from 150 to 270° C., a pressure in the range from 150 to 390 bar and in the presence of a chromium-free heterogeneous catalyst comprising copper.

2. The process according to claim 1, wherein the reaction is carried out continuously at a space velocity over the catalyst in the range from 0.01 to 5.0 kg of dialkyl oxalate (I)·$liter_{cat.}^{-1} \cdot h^{-1}$.

3. The process according to claim 2, wherein the space velocity over the catalyst is set so that the conversion of dialkyl oxalate (I) is ≥90%.

4. The process according to claim 1, wherein the reaction is carried out continuously in a reactor at a cross-sectional loading in the range from ≥10 to 1000 m/s.

5. The process according to claim 1, wherein the reaction is carried out continuously in a reactor at a cross-sectional loading in the range from >10 to 500 m/s.

6. The process according to claim 1, wherein dialkyl oxalate (I) and $H_2$ are used in a molar ratio of $H_2$:dialkyl oxalate (I) in the range from 4.2 to 20.

7. The process according to claim 1, wherein dialkyl oxalate (I) and $H_2$ are used in a molar ratio of $H_2$:dialkyl oxalate (I) in the range from 4.3 to 15.

8. The process according to claim 1, wherein the reaction is carried out at a temperature in the range from 170 to 260° C.

9. The process according to claim 1, wherein the reaction is carried out at a pressure in the range from 160 to 290 bar.

10. The process according to claim 1, wherein the reaction is carried out continuously in a reactor and the reactor is operated with recycle by part of the reactor output being recirculated from the reactor outlet to the reactor inlet.

11. The process according to claim 1, wherein the dialkyl oxalate (I) is dimethyl oxalate.

12. The process according to claim 1, wherein the copper-comprising heterogeneous catalyst comprises aluminum oxide.

13. The process according to claim 1, wherein the heterogeneous catalyst comprises lanthanum oxide.

14. The process according to claim 1, wherein the heterogeneous catalyst comprises from 10 to 80% by weight of copper, from 0.5 to 20% by weight of lanthanum oxide and from 19.5 to 89.5% by weight of aluminum oxide.

15. The process according to claim 1, wherein the solvent is methanol, ethanol, n-propanol, isopropanol and/or ethylene glycol.

16. The process according to claim 1, wherein the reactor is a shell-and-tube reactor or shaft reactor.

17. The process according to claim 1, wherein the catalyst is arranged as a fixed bed in the reactor.

* * * * *